(12) United States Patent
Sauer

(10) Patent No.: US 8,034,010 B1
(45) Date of Patent: Oct. 11, 2011

(54) PROGRESSIVE RESISTANCE KNEE PAD

(76) Inventor: Irwin William Sauer, Costa Mesa, CA (US)

( * ) Notice: Subject to any disclaimer, the term of this patent is extended or adjusted under 35 U.S.C. 154(b) by 19 days.

(21) Appl. No.: 12/642,735

(22) Filed: Dec. 18, 2009

Related U.S. Application Data

(60) Provisional application No. 61/203,150, filed on Dec. 20, 2008.

(51) Int. Cl.
  *A61F 5/00* (2006.01)
  *A61F 5/24* (2006.01)
  *A41D 13/00* (2006.01)

(52) U.S. Cl. .................. 602/16; 128/95.1; 2/24

(58) Field of Classification Search .............. 128/95.1, 128/112.1, 115.1, 116.1, 121.1, 124.1, 122.1, 128/123.1, 126.1; 602/32, 1, 5, 23, 26, 16, 602/13, 24, 25; 2/24, 62, 267, 411, 455
See application file for complete search history.

(56) References Cited

U.S. PATENT DOCUMENTS

| | | | | |
|---|---|---|---|---|
| 7,857,776 | B2 * | 12/2010 | Frisbie | ..................... 602/12 |
| 2007/0276305 | A1 * | 11/2007 | Kahlmeyer et al. | ............. 602/23 |

\* cited by examiner

*Primary Examiner* — Patricia Bianco
*Assistant Examiner* — Tarla Patel
(74) *Attorney, Agent, or Firm* — James F. Kirk

(57) ABSTRACT

A progressive resistance knee pad coupled to the inner surfaces of a knee brace to prevent metal components of an orthotic support from contacting clothing, tissue or skin surface of the wearer of the orthotic support appliance. The knee pad has a cushion layer having a contoured contact surface and a support surface. A middle layer has a mating surface and a middle layer base surface. A base layer has a top surface and a mounting surface. An imbedded mounting plate has uniform thickness and is imbedded in the base layer. The middle layer support surface is formed to shape the cushion layer contact surface to conform with a contoured surface. The thickness of the middle layer is controlled and adjusted to provide a substantially planar middle layer base surface. The base layer imbedded mounting plate is characterized to receive fastening means for coupling the progressive resistance knee pad to the appliance.

15 Claims, 9 Drawing Sheets

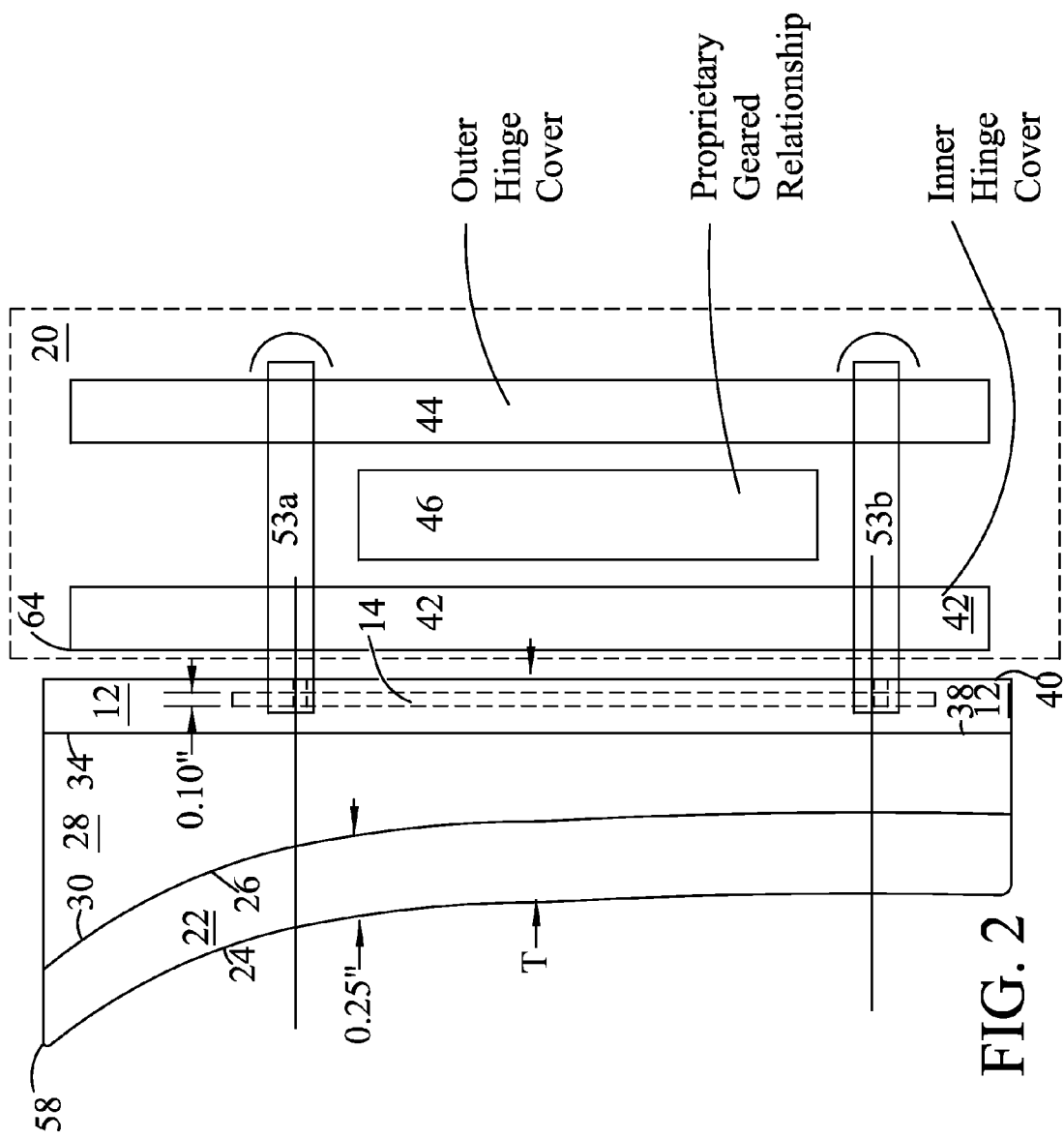

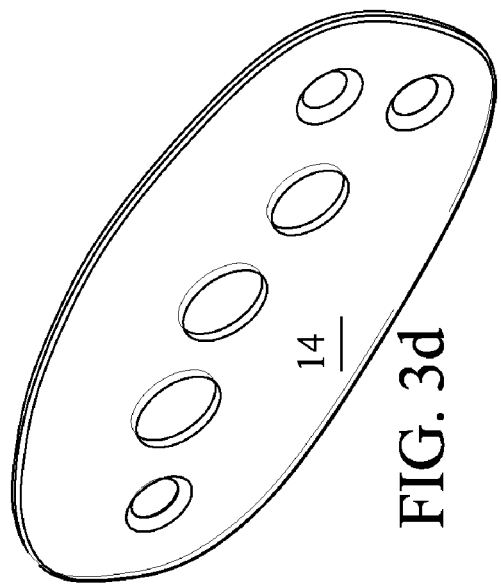
FIG. 3b
FIG. 3d
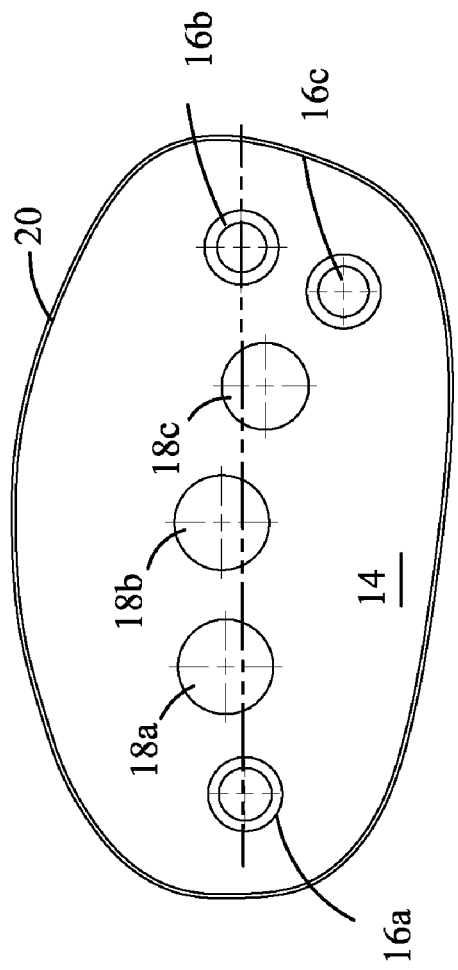
FIG. 3a
FIG. 3c

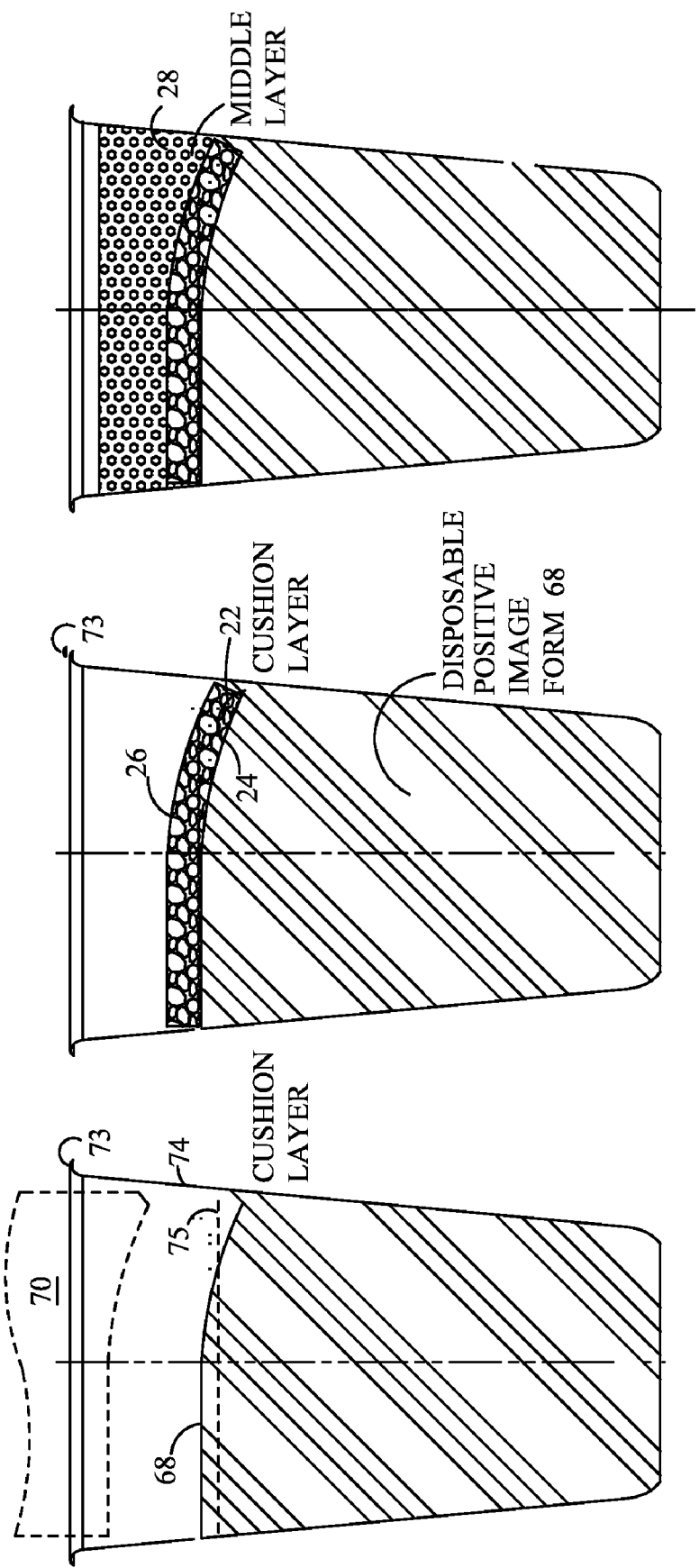

# PROGRESSIVE RESISTANCE KNEE PAD

This application is a CIP of and claims priority from provisional patent application Ser. No. 61/203,150 filed Dec. 20, 2008 for a Progressive Resistance Knee Pad and having a common inventor.

BACKGROUND

1. Field of Invention

This invention relates to the field of orthotic appliances such as knee braces and more particularly to the padding found on the inner surfaces of knee braces that prevent metal components of the orthotic support from contacting the clothing, tissue or skin surface of the wearer of the orthotic support appliance. Knee braces relating to this invention include those having at least one hinge assembly that are designed to apply a lateral force to a portion of the leg (typically the knee) to align the lower portion of the leg with the upper portion of the leg. The field of knee braces of interest include knee braces of the un-loader type which have a single hinge and knee braces that have two hinges, one hinge being on the inner (medial) surface of the leg and a second hinge on the outer (distal) surface of the leg.

2. Related Art

Knee pads found on presently available orthotic appliances such as the knee braces by the Townsend Corp. of Bakersfield Calif. are presently formed from a single stage resistance material and are covered with cloth to prevent contact and to provide a cushion between the wearer's knee tissue and the appliance. A single stage material having a uniform hardness and stiffness is typically used. The cushion is formed from a polymeric foam which is not custom fitted to the contour of the knee region of the leg of the wearer. Such pads or cushions are coupled to the appliance using adhesive backed Velcro fastening material. Over time, and with use, such pads loosen and fall off of the appliance.

Another disadvantage associated with knee pads found on presently available appliances is that they have a tendency to permanently deform and collapse thereby failing to provide the support and cushion originally intended.

SUMMARY OF THE INVENTION

This invention is of use with the dual hinge knee brace where the brace typically applies equal net compressive forces to the upper and lower portions of the leg while simultaneously applying a net equivalent force to the knee in a lateral direction opposite to the forces being applied to the upper and lower leg. The net lateral force against the lower being in the direction necessary to guide the lower portion of the leg into proper alignment with the upper portion of the leg. The sum of the lateral force applied to the knee is equivalent to the sum of the combined lateral but opposite in direction force applied to the upper and lower portion of the leg. The invention progressive resistance knee pad distributes the load that would normally be transferred from the hinge assembly to an inner or outer surface of the knee of the patient using the knee brace without a tendency to collapse or break loose in response to shear loads between the hinge and the patient's knee.

The progressive resistance knee pad is coupled to the inner surfaces of a knee brace or hinge assembly of the knee brace to prevent metal components of an orthotic support from contacting clothing, tissue or skin surface of the wearer of the orthotic support appliance. The progressive resistance knee pad has a cushion layer having a contoured contact surface and a support surface. A middle layer has a mating surface and a base surface. A base layer has a top surface and a mounting surface. An imbedded mounting plate has uniform thickness and is imbedded in the base layer. The middle layer support surface is formed to shape the cushion layer contact surface to conform with a contoured surface. The thickness of the middle layer is controlled and adjusted to provide a substantially planar base surface. The base layer imbedded mounting plate is characterized to receive fastening means for coupling the progressive resistance knee pad to the appliance. It should be clear that when mounting the progressive resistance knee pad to the inner surface of a hinge assembly, it may be necessary to remove or clear a factory supplied knee pad or coating from the hinge assembly so as to provide a proper base on which to mount and secure the progressive resistance knee pad.

BRIEF DESCRIPTION OF THE DRAWINGS

FIG. 2 is a schematic sectional view of the progressive resistance knee pad of FIG. 1 taken on section line 2-2;

FIG. 3a-3d are four views of an example of a mounting plate after fabrication from a blank and prior to being imbedded in a base layer.

FIG. 5a is a schematic sectional view of a disposable cup, typically a plastic cup with a straight horizontal dashed line showing a first level of wet plaster in phantom, a negative of a disposable positive image form above the cup is shown in phantom and the resulting disposable positive image form is shown in the disposable cup as a solid line as a result of the negative image form being pressed into the first level of wet plaster in phantom to form the disposable positive image form;

FIG. 5b is a schematic sectional view of a disposable cup containing a disposable positive image form with a contact surface of a cushion layer forced to assume the contour of the disposable positive image form;

FIG. 5c is the schematic sectional view of FIG. 5b with material for the middle layer on top of the cushion layer;

DETAILED DESCRIPTION OF THE INVENTION

Figure 1:
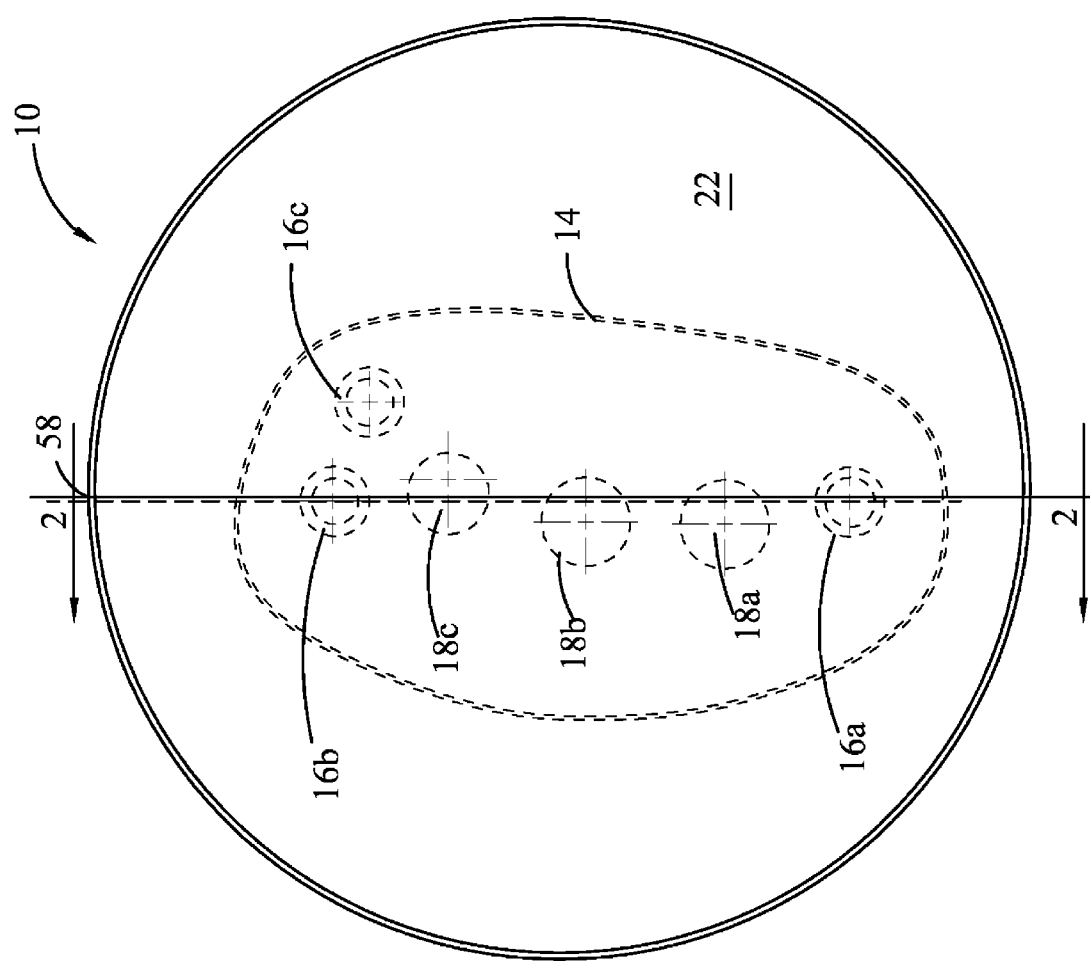
FIG. 1 is schematic plan view of a first embodiment of the invention progressive resistance knee pad viewed from the surface in contact with the patient's knee.

FIGS. 1 and 2 respectively show the principal features of the progressive resistance knee pad 10 with FIG. 1 being a plan view of the progressive resistance knee pad 10, looking at the cushion layer contact surface that bears against the patients knee, with a base layer 12 hidden in the layers below the visible layer. The base layer 12 appears in FIG. 2 and has an imbedded mounting plate 14 that appears in phantom in each of the two figures. The base layer 12 is typically cast from a polymer casting material such as urethane. The process of casting the base layer 12 typically precedes assembly of the progressive resistance knee pad 10. The imbedded mounting plate 14 is imbedded in the base layer 12 before the base layer 12 is used to form the progressive resistance knee pad 10.

FIG. 1 depicts AN outline shape of the imbedded mounting plate 14 as being quasi oval; however, the shape shown is an arbitrary choice and is a design choice that is based on the size of the progressive resistance knee pad 10 that is being made, and the points of attachment to the knee brace (or orthotic appliance) for which it is being made.

FIG. 2 schematically shows the composite structure of the invention progressive resistance knee pad 10 attached to the schematic sectional view of a (right leg) hinge housing, represented by phantom box 20. The view shown is that of a progressive resistance knee pad 10 used on the inside of a right leg brace (not shown).

The invention progressive resistance knee pad 10 is shown having three layers. A first layer, cushion layer 22, is made from a cushion material and has a contoured cushion layer contact surface 24 and a cushion layer support surface 26. The cushion layer 22 is formed from a first predetermined Durometer material such as a silicon sheet material that has a Durometer Shore A value of 20. The cushion layer 22 is formed from sheet material that has a uniform thickness of typically 0.25 inches and can be purchased from the McMaster Carr Co. of Los Angeles with four locations elsewhere in the United States. When a liquid version of this material becomes available, it may offer advantages for its use over the sheet stock now in use. A liquid version of a material with properties matching those of the sheet stock would permit the cushion layer to be cast on the disposable positive image form 68 that will be discussed later in this disclosure.

The second or middle layer 28 has a mating surface 30 and a middle layer base surface 34. The middle layer 28 is formed from a silicon adhesive, such as Dow Corning 739 available from McMaster Carr.

The third or base layer 12 is shown having a base layer top surface 38 and a base layer mounting surface 40. An imbedded mounting plate 14 is shown in phantom in FIGS. 1, 2, 5e and 8.

Figure 4:
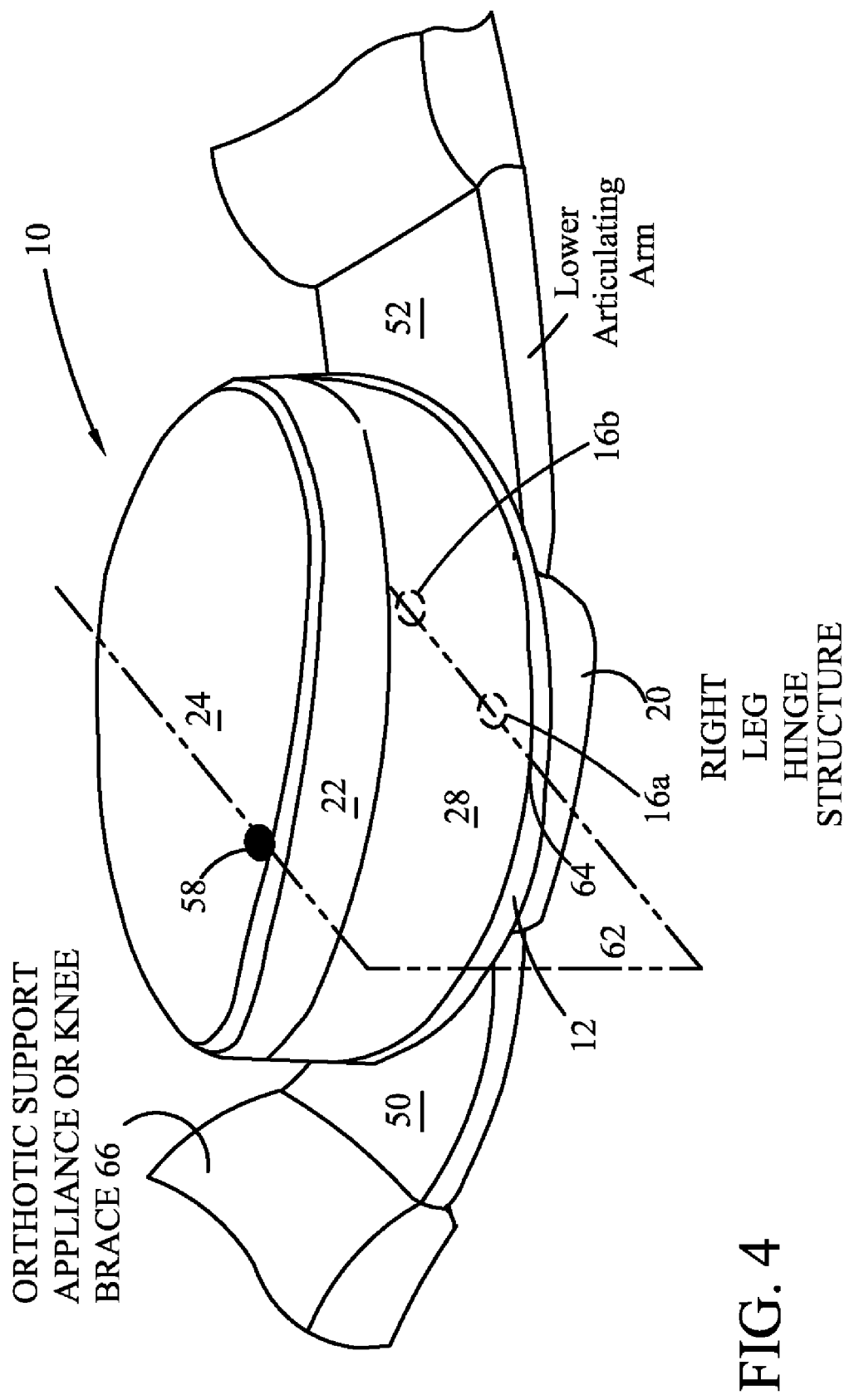
FIG. 4 is a perspective view showing the invention progressive resistance knee pad coupled to a portion of the hinge housing of an orthotic apparatus.
Figure 5E:
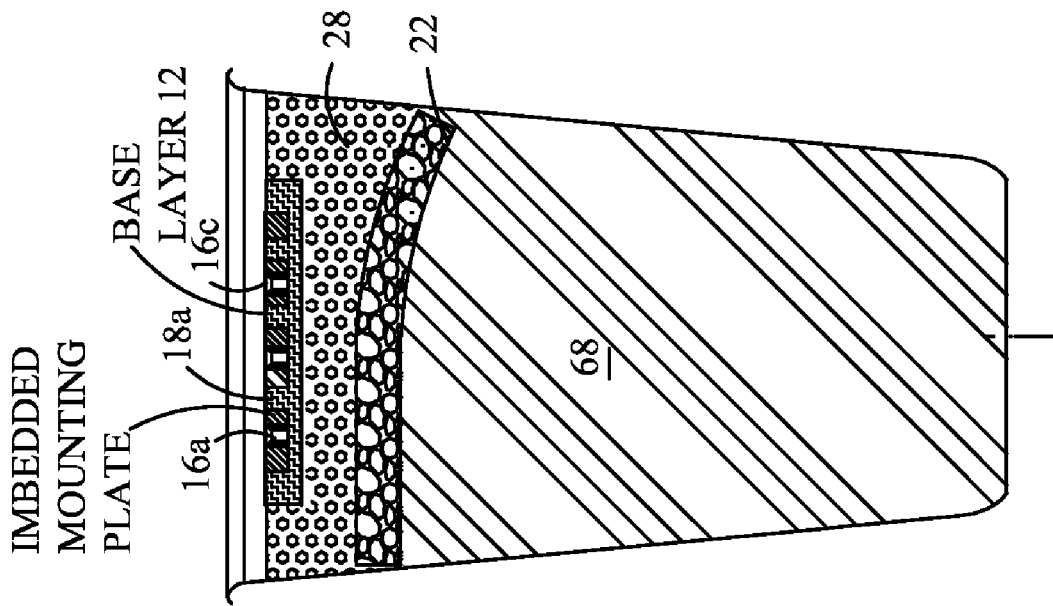
FIG. 5e is a schematic sectional view of FIG. 5d with a base layer shown having an imbedded mounting plate formed in the base layer.
Figure 5D:
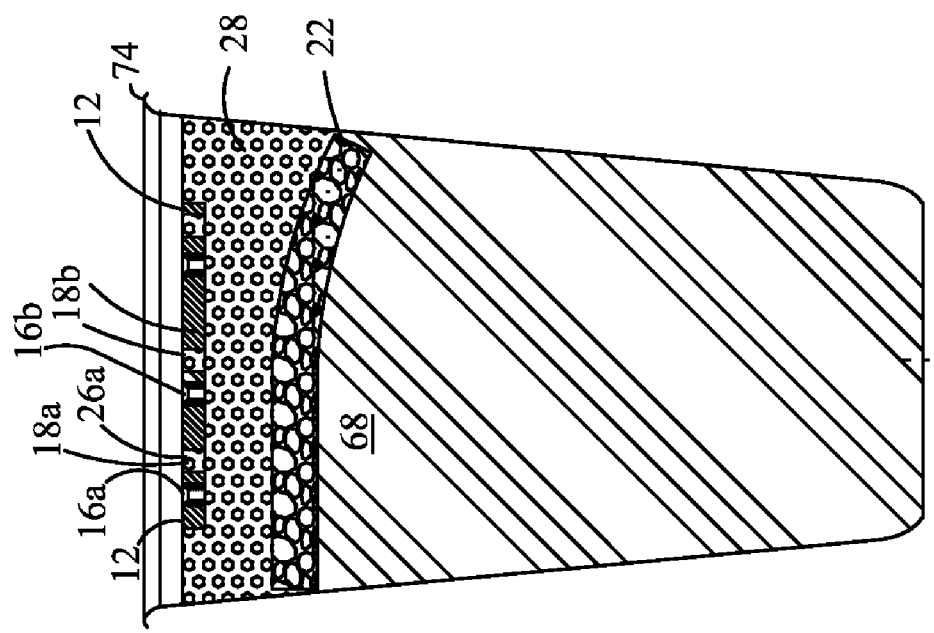
FIG. 5d is a schematic sectional view of FIG. 5c with a mounting plate pressed into the middle layer to serve as a base layer.

The three layers of the progressive resistance knee pad 10 are bonded together to form a composite or layered structure in a final molding process. Referring to FIGS. 2 and 4, the right leg hinge housing contained within phantom box 20 has an inner hinge cover 42 and an outer hinge cover 44. Box 46 is a schematic representation of a proprietary geared relationship 46, provided by the knee brace or hinge housing 20, in section that joins the upper articulating arm 50 and the lower articulating arm 52 held between the inner and outer hinge covers 42, 44. The articulating arms 50, 52 meet and function with the proprietary geared relationship 46 being treated as an off the shelf component supplied by the manufacturer of the hinge housing 20. Threaded screws 53a and 53b pass through the hinge covers 42, 44 and anchor into the imbedded mounting plate 14 coupling the progressive resistance knee pad 10 to the hinge housing 20.

FIG. 3 shows the mounting plate 14, before imbedding in the base layer, having threaded screw holes 16a, 16b and 16c. Three post mooring holes 18a, 18b and 18c in the imbedded mounting plate 14 permit the casting material from which the base layer 12 is formed to flow through and fill the post mooring 18a, 18b and 18c holes in the imbedded mounting plate 14. When the casting material hardens, the post mooring holes 18a, 18b and 18c provide support for the imbedded mounting plate against shear forces transmitted via the base layer 12.

Axial Alignment of the Progressive Resistance Knee Pad

FIG. 4 is a perspective view that shows a knee brace or a hinge housing 20 to which a progressive resistance knee pad attached.

A rotational alignment of the progressive resistance knee pad 10 with the right leg hinge housing 20 is achieved by aligning the forward most point of the cushion layer 58, of the progressive resistance knee pad 10, as shown in FIGS. 1, 2 and 4 with the forward most point or edge of the leg hinge housing 64. The forward edge and foremost point of the of the (right) leg hinge housing is established schematically in FIG. 4 by a phantom plane 62 that is shown passing through threaded screws 53a, 53b which pass through the outer and inner hinge covers 42, 44, located by the threaded screw holes 16a, 16b to anchor in the imbedded mounting plate 14.

The leg hinge housing 20 of leg braces from other suppliers may have alternative screw locations but aligning the location of the forward most point of the leg hinge housing 64 with the forward most part of the cushion layer 58 is believed to be well within the skill of practicing orthotists. The lower and upper articulating arms 50, 52 that articulate and are coupled together via the proprietary geared relationship 46 are products of an appliance supplier such as the one in FIG. 4 that was supplied by Townsend Designs Inc. of Bakersfield, Calif.

As shown in FIG. 4, the invention knee pad 1 is coupled to a portion of a hinge housing 20 on the inner surfaces of an orthotic support appliance 66 (partially shown) to prevent the metal components of the orthotic support appliance from contacting clothing, tissue or skin surface (not shown) of the wearer of the orthotic support appliance 66. The invention progressive resistance knee pad 10 is coupled to the orthotic support appliance 66 with a number of threaded screws 53a, 53b as shown in FIG. 2, that pass through the hinge housing 20 of the orthotic support appliance 66 to the imbedded mounting plate 14. A method for making an imbedded mounting plate follows.

Fabricating the Imbedded Mounting Plate for the Base Layer

FIG. 3a shows the imbedded mounting plate 14 in a conventional plan view. FIG. 3b shows the imbedded mounting plate in a right side or right edge view and FIG. 3c shows the imbedded in a front edge view. FIG. 3d show the imbedded mounting plate in a perspective view. The plate shown typically has a uniform thickness. The blank selected for the embodiment of FIGS. 3a-3d has a thickness between the limits of 0.010 and 0.375 inches.

The step of making an imbedded mounting plate 14 begins with the step of providing a blank plate suitable in size and thickness for the purpose. In the example of FIG. 3a-3d, an irregular shaped or piece of sheet aluminum (type 6061) was selected for the application. The threaded screw holes 16a, 16b and 16c are positioned to mate with the existing threaded screw holes (schematically shown in phantom in FIG. 4) that are on the knee brace hinge housing 20 that will be using the progressive resistance knee pad 10.

With reference to FIG. 2, the process of the location and alignment of at least two of the threaded screw holes in the imbedded mounting plate 14 in the base layer 12, with the threaded screws 53a, 53b that pass through hinge housing 20 for which the progressive resistance knee pad is being made, begins with the steps as follows: A technician removes a first of the threaded screws that the manufacturer of the hinge housing 20 supplied to hold the inner hinge plate cover 42 or its equivalent, and outer hinge plate cover 44 or its equivalent in position with respect to a the planned location for threaded screw hole 16*a* on the imbedded mounting plate 14. The blank is then centrally or coaxially located on the surface of the inner hinge cover 42, the location of a threaded screw hole is marked on the blank plate to aid in locating the threaded screw hole 16*a*. When thus marked, the blank plate is drilled and tapped to receive a first elongated threaded screw 53*a*.

The first elongated threaded screw is installed to hold the blank plate for the imbedded mounting plate 14 on the surface of the inner hinge cover 42 on the hinge housing 20. The blank plate is rotationally positioned to align the blank plate so that the second threaded screw hole location can be marked using a second elongated threaded screw. The preceding process is repeated as required for each of the remaining threaded screw holes 16*b*, 16*c* as may be required. The threaded screws are removed in sequence, each screw being replaced by an elongated threaded screw.

With a set of replacement elongated screws installed the plate is marked to identify the forward most location on the knee brace 42 so that it may later be aligned with the base layer top surface 38 to obtain alignment of the base layer 12 with the forward most point of the cushion layer 58.

Fabricating the Base Layer

The base layer 12 is formed as a subassembly before the molding process of the progressive resistance knee pad 10 is started. The base layer 12 must exist and be available to support the molding process whether the process selected for molding the progressive resistance knee pad uses a solvent evaporation process as suggested by FIGS. 5*a*-5*d*, 6 and 7 or the catalyzed process of FIG. 8.

The base layer 12 is formed by mixing together a urethane or two part casting compound (such as type 60A liquid) using the 60A base and 60A activator from Forsch Polymer Corp. of Englewood, Colo. to form a premixed liquid (an uncured urethane two part mixture), in a first disposable container (not shown) for that purpose. A portion of the premixed liquid two part casting compound is then poured or loaded into a second disposable container (not shown) that will contain a mold for the base layer or that will be capable of serving as mold or molding container for the base layer 12.

Elongated screws (not shown) are then screwed into the previously prepared threaded screw holes 16*a*, 16*b* and 16*c*, shown schematically in FIG. 3*a*-3*d*, to serve as handles for guiding the imbedded mounting plate 14 into the urethane loaded mold for the base layer 12 (not shown). As explained above, the mounting plate 20 has a plurality of additional post mooring holes 18*a*, 18*b* and 18*c* through which the uncured urethane mixture flows and later hardens to assist in anchoring the mounting plate 20 into the casting that is to become the base layer 12. Using the elongated screws extending from threaded screw holes 16*a*, 16*b* and 16*c*, a technician manually guides the imbedded mounting plate 14 into the urethane loaded mold to a predetermined depth, typically to a point where the surface of the imbedded mounting plate 14 is flush with or slightly below the base layer mounting surface 40. The technician releases the elongated screws passing through the imbedded mounting plate 14 and the top of what will become the base layer 14 with the base layer mounting surface 40 exposed in the mold. In an alternative embodiment, sheet metal screws can be substituted for threaded screws.

Although not shown in the drawings, in another alternative method, the elongated screws can be inserted into the imbedded mounting plate 14 so as to extend through the mounting plate 20 to serve as a depth stop or depth gage to locate the mounting plate at a predetermined position in the mold material for the base layer 12. An additional amount of the uncured urethane two part mixture is then poured onto the top surface of the imbedded mounting plate 14 residing in a mold to increase the thickness of the base layer 12 to an initial predetermined thickness.

After the two part urethane mixture hardens, a now preformed base layer 12 with the imbedded mounting plate 14 therein, is removed from the second disposable cup or disposable mold in which the base layer 12 was cast. The elongated screws are removed from the base layer 12. The base layer 12 mounting surface 40 and the base layer top surface 38 can then be machined to obtain a base layer 12 having a final predetermined thickness if the required tolerances so dictate.

Preparation of Disposable Knee Cast

In each method for making a progressive resistance pad 10 for use on a patient's knee, a casting is first made of the patient's knee. The casting of the knee is hereinafter called a negative image (not shown) with the patient's lower leg extended as it might be while standing. The casting process uses plaster or similar fast drying material to fabricate the negative image form (not shown) of the surface of the knee. The negative image form or casting is then used to make a disposable positive image form 68 or casting of the patient's knee. As shown in FIG. 5*a*, the disposable positive image form 68, of the knee is then placed in the bottom of a disposable cup mold 74 to serve as a mold for the progressive resistance knee pad.

An alternative method for making a disposable positive image form 68 in the bottom of a disposable cup 74 begins with loading a portion of the cup with wet fast drying material, and then pressing a corresponding negative image form, shown in FIG. 5*a* as a schematic phantom outline 70 downward into the exposed surface 75 of the fast drying material, shown as a level phantom line, forcing the fast drying material into the negative form 70 to form a positive image of the knee in the exposed surface of the fast drying material 75. The positive image is represented by a solid image curve in FIG. 5*a*. The casting with the positive image in its upper surface that remains in the cup is a disposable positive image form 68.

FIG. 2 schematically shows the thickness of the progressive resistance knee pad as dimension T. The thickness T for each progressive resistance knee pad will vary as a function of patient requirements and will be established as a thickness value equal to or greater (to establish a slight pre-load) than the physical distance between the surface of the patients knee and the location of the inner surface of the hinge (i.e. the gap there-between). The thickness T is typically measured with the knee brace on the patient without padding present in a sitting position with the leg of the patient in a near but not full extension position. An additional thickness is added to the measurement of thickness less an allowance for clothing to the measurement T to assure a suitable preload on the leg from the knee brace when in service. The final value of T is determined with consultation and assistance of an orthotist that the patient has selected or been directed to. The final mold for the progressive resistance knee pad 10 will use the disposable positive image form 68 in the disposable cup mold 74 with a cushion layer that has uniform thickness and that is held against the positive image form 68 but is not bonded with adhesive to the exposed surface of the disposable positive image form 68.

A Method for Molding the Progressive Resistance Knee Pad Using a Disposable Mold and Solvent Evaporation System Referring to FIG. 5a, the molding process begins with a first step of providing a disposable positive image form 68 using a method such as one of those described above or possibly one using laser modeling.

The disposable positive image form 68 is placed in a progressive resistance knee pad mold, (typically a disposable cup mold 74 with a cup lip 73 such as that shown in FIG. 5a. There may be an uncertainty of the depth to which the disposable positive image form 68 descends into the disposable cup mold 74. As the disposable positive image form 68 is positioned in the disposable cup mold 74, the distance between the center surface of the disposable positive image form 68 and the surface or a plane established by the cup mold lip 73 is measured to establish a depth D. A depth Q is then determined as the difference between the depth D and the desired end thickness dimension T as the depth required below the lip of the mold 27 at which the base layer mounting surface 40 of the base layer 12 will be allowed to rise as material for middle layer 28 is added into the disposable cup mold 74. An allowance is made for the thickness of the later addition of the base layer 12 as the depth Q is determined and marked on the disposable cup mold 74.

Figure 6:
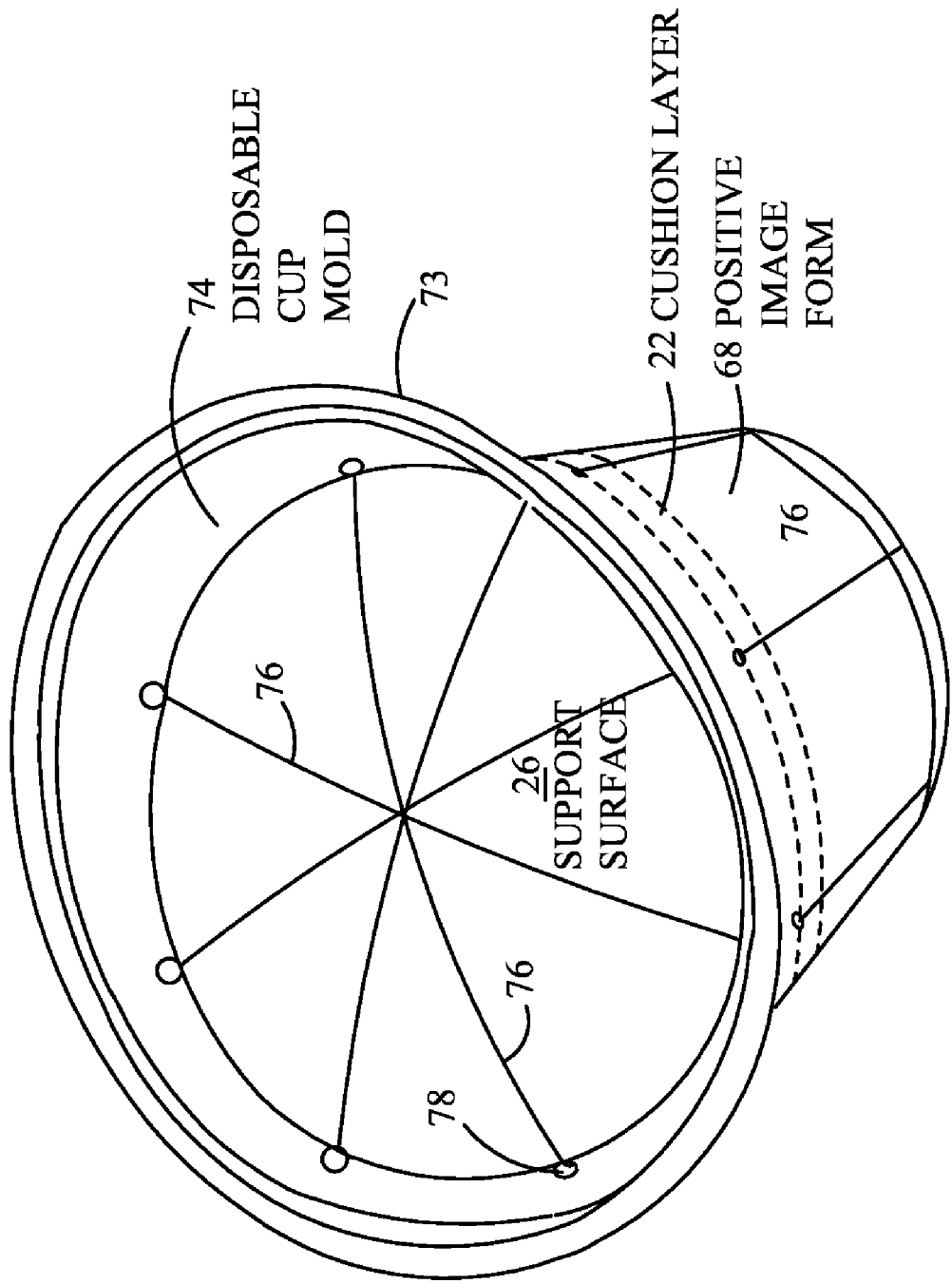
FIG. 6 is a top-down perspective view of a disposable cup mold (a plastic cup) in which an array of threads are positioned to hold a cushion blank against a plaster male casting of the patient's knee that form a disposable positive image form visible through a lower portion of the disposable cup mold.
Figure 7:
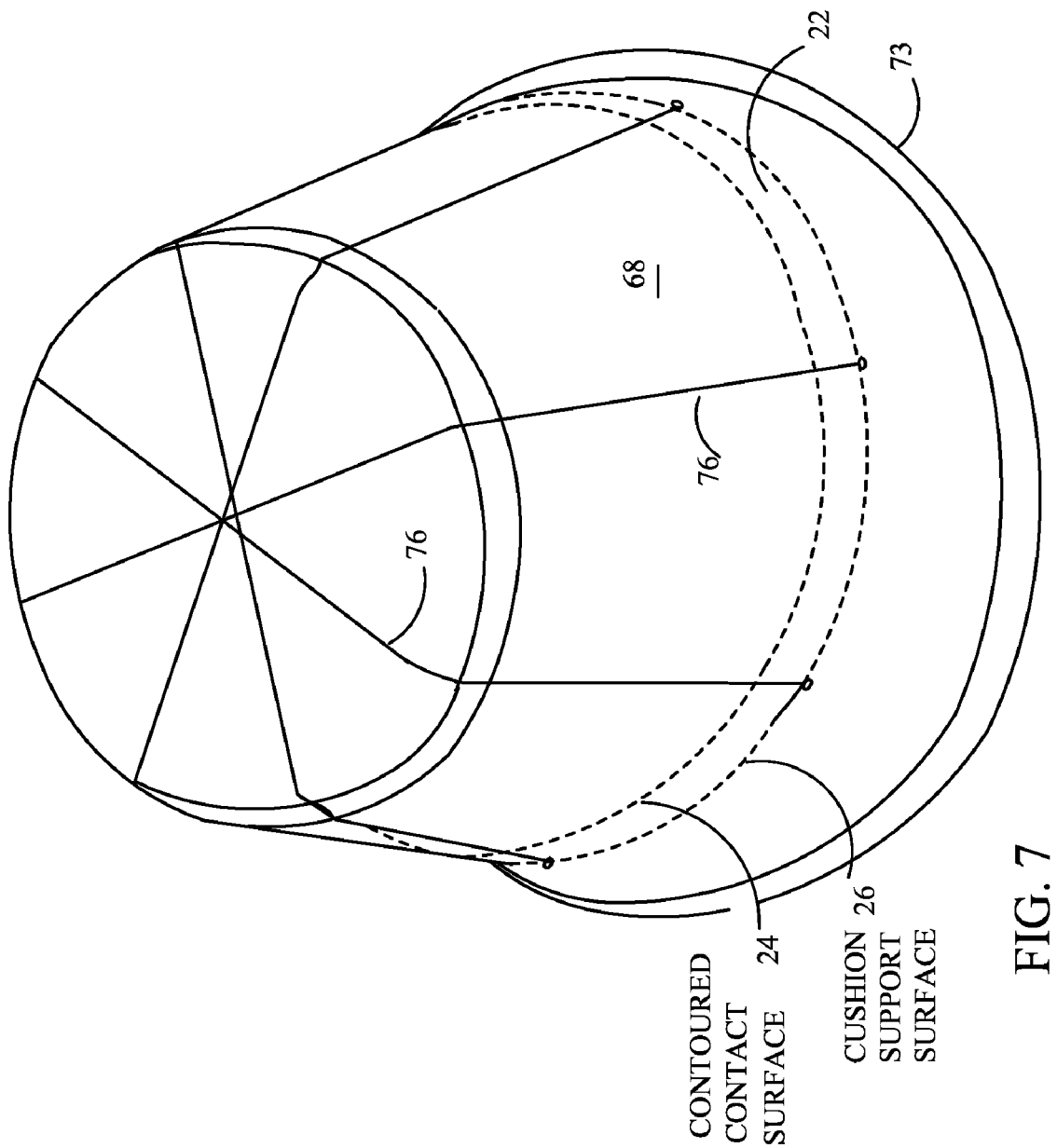
FIG. 7 is a perspective view of the disposable cup (a plastic cup) mold of FIG. 6 showing the under side of the disposable cup mold.

A blank of the cushion layer 22 is then cut from sheet material. As shown in FIGS. 6 and 7, the blank to be formed into the cushion layer is then held against the surface of the disposable positive image form 68 using a plurality of thin evenly distributed threads 76. Nylon thread has been used and found to be satisfactory. However other similar thread material that has sufficient strength can be substituted for Nylon. The threads 76 are installed as shown in FIG. 6 in a quasi circular array in tension. Each thread 76 passes across the center of the support surface of the cushion layer blank and then past the outer periphery of the disposable positive image form 68 through a small hole 78 in the side of the disposable cup mold 74 so as to compress the cushion layer support surface 26 of the cushion blank against the surface of the exposed surface of the disposable positive image form 68. The threads 76 are then held in uniform tension outside of the disposable cup mold 74 or final form that will define the perimeter of the progressive resistance knee pad 10.

A silicon adhesive, such as Dow Corning 739 available from McMaster Carr, is then layered onto the previously assembled cushion layer blank to the previously marked depth Q, the nylon threads 76 still being in place, the cushion layer blank being secured to the positive knee casting or disposable positive image form 68 with its perimeter bounded by the walls of the disposable cup mold 74. The upper surface of the middle layer 28 in contact with the room air forms the middle layer base surface 34.

A silicon adhesive, such as Dow Corning 739 available from McMaster Can, is then layered onto the previously assembled cushion layer blank to the previously marked depth Q, the nylon threads 76 still being in place, the cushion layer blank being secured to the positive knee casting or disposable positive image form 68 with its perimeter bounded by the walls of the disposable cup mold 74. The silicon adhesive casting process inherently forms the middle layer as a homogenous and void free layer with a varying cross section on the cushion layer. The silicone adhesive casting results in the middle layer mating surface forming a contiguous and congruent bond with the cushion layer support surface.

FIG. 4 shows a phantom plane 62 sketched onto the embodiment to schematically show that threaded screw holes 16a, 16b or other like index can be used to link the alignment of the base layer 12 for later registration with the forward most point of the leg hinge housing 64 as the base layer 12 is positioned into the material of the middle layer 28 and rotated for alignment with the forward most point of the cushion layer 58 so that when assembled onto the knee brace, the progressive resistance knee pad 10 will be orientated rotationally to provide a proper predetermined separation between the patient's skin and the metal of the hinge housing 20 or knee brace.

Using the materials mentioned, curing of the composite structure in the disposable cup mold 74 can take as long as ten days under normal room conditions. However, the preceding construction method requires no additional bonding agents between the various surfaces.

An initial major problem was encountered in obtaining good adhesion between silicon cushion layer 22 and the middle layer 28. A Silicon compound was located and is now used that obtains a preferred value of Durometer. The silicon material that was selected is Dow Corning 739 which was found to provide good adhesion to the cushion layer 22 material.

As shown in FIG. 2, the middle layer 28 is formed to have a varying cross section. The middle layer mating surface 10 is contiguous with the cushion layer support surface 26. In addition, the middle layer mating surface 30 is formed to shape or copy the cushion layer contact surface 24 or to conform with the contoured surface of the cushion layer 22. The thickness of the middle layer 28 is controlled and adjusted to provide a substantially planar middle layer base surface 34. The base layer top surface 38 is contiguous with the middle layer base surface 34.

The base layer imbedded mounting plate 14 as shown in FIG. 2 is characterized to receive fastening means, such as threaded screws 22a and 22b via threaded screw holes 16a and 16b respectively for coupling the progressive resistance knee pad 10 to the hinge housing 20. Additional threaded screw hole 23c is shown in FIG. 3 and receives a threaded screw (not shown) in FIGS. 1 and 2.

The base layer 12 is formed from a material having a Durometer value material that is higher than the Durometer value of the material of the middle layer 28. In the preferred embodiment, the base layer 12 has a Durometer value of Shore A 60. The middle layer 28 is further characterized as being formed from a material having a Durometer value of Shore A 37. The value quoted here appears on the specification sheet published by Dow Corning for Dow Corning 739 material. The base material is a Frosch Polymer Corporation product that can be found in the McMaster Catalog. The material has a Durometer Shore A value of 60 that appears in a data sheet for the material.

Figure 8:
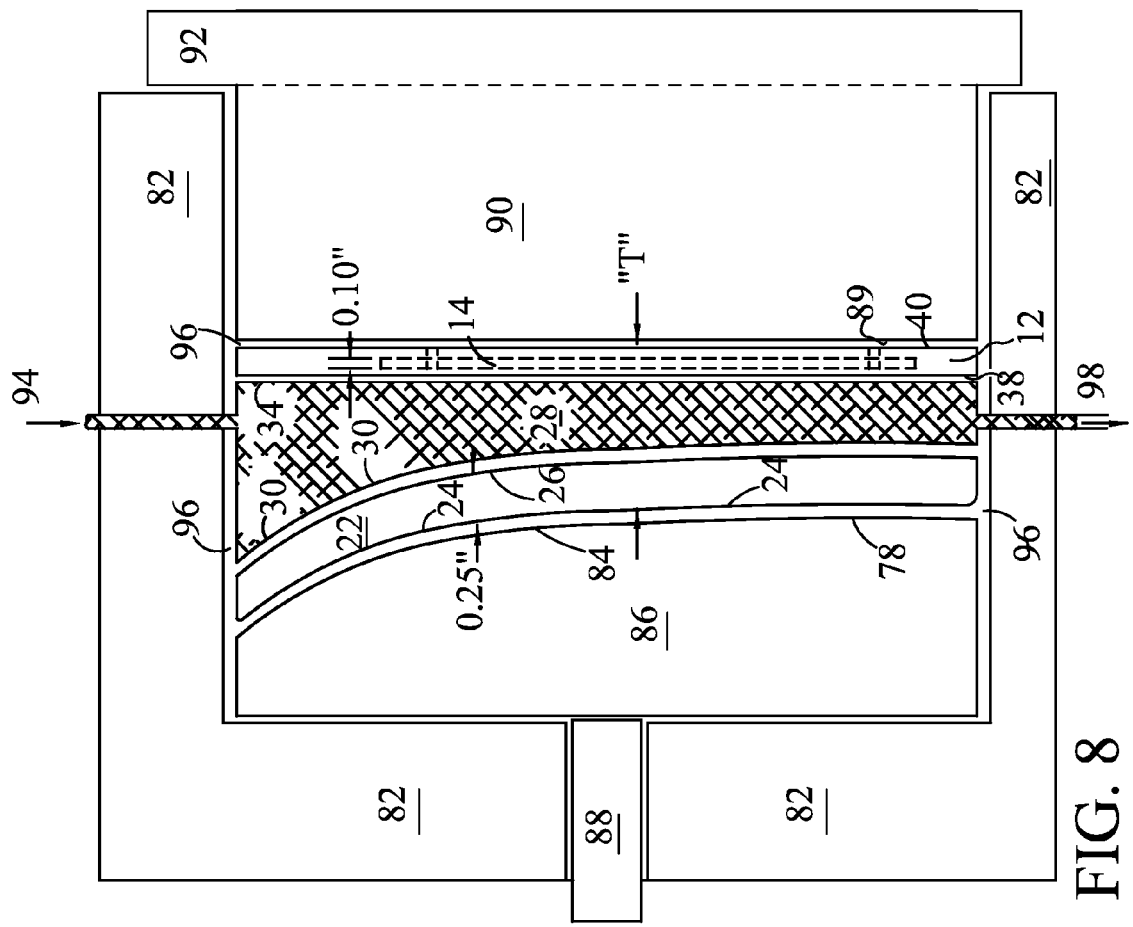
FIG. 8 is a schematic sectional view of a reusable mold for making a progressive resistance knee pad.

Molding the Progressive Resistance Knee Pad Using a Reusable Mold and a Catalyzed Silicon System FIG. 8 shows a schematic cross sectional view of a reusable mold 82 used in a method for producing the progressive resistance knee pad 10 with similar components and properties as described for the progressive resistance knee pad in the previous sections, but with the elimination of the plastic cup and the array of nylon threads 76 used to hold the cushion layer 22 against a predetermined contoured surface 84 that is positioned on a positive image form 86. The reusable mold 82 is fitted with an ejection rod 88 and a retention ram 90. The retention ram 90 has a stop flange 92 fitted to the external end at the right of the figure. The stop flange 92 provides a travel limit for the retention ram 90 for the purpose of positively limiting the depth that the retention ram 90 travels into the reusable mold 82 cavity 96. In another embodiment, the stop flange 92 is replaced by a threaded ring that is screwed onto the retention ram 90 to limit the depth to which the retention ram 90 travels and to make that depth adjustable. Other means for adjusting the depth to which the retention ram 90 travels with respect to the positive image form 86 would include using shims between the stop flange 92 and the ends of the reusable mold 82 or under the positive image form 86.

The reusable mold 82 also provides a liquid component inlet tube 94 through which a two-component silicone elastomer is delivered to a cavity 96 for forming the middle layer 28. Relief tube 98 is shown on a wall opposing the location of the inlet tube 94. The relief tube 98 provides a path though which air and excess elastomer is vented or released as the cavity is filled.

The predetermined contoured surface 84 on the positive image form 86 forms the cushion layer contact surface 24 of the progressive resistance knee pad 10. The cushion layer contact surface 24 is the external surface of the composite three layer structure that comprise the progressive resistance knee pad 10. In FIG. 8 gaps appear between the layers so that surfaces on the layers and surfaces of the mold can be identified. It should be understood that the gaps shown in FIG. 8 are illustrative (as in a partially exploded view) and that when the composite three layer structure is being formed, the gaps are not present. As previously characterized above with respect to FIG. 2, the Cushion layer 22 has a contoured cushion layer contact surface 24 and a cushion layer support surface 26 which are identified more clearly in FIG. 8 where gaps are schematically provided between the layers. The middle layer 28 shown with cross hatching, has a middle layer mating surface 30 and a middle layer base surface 34.

The Base layer 12 is shown having a base layer top surface 38 and a base layer mounting surface 40. An imbedded mounting plate 14 is shown in phantom in FIG. 8 as it was also shown in FIGS. 1, 2 and 5e.

The apparatus shown in FIG. 8 is used with the following method: A predetermined contoured surface 84 is formed on the surface of a positive image form 86. The predetermined contoured surface 84 is exposed in the cavity 96 of the reusable mold 82.

The bottom of a positive image form 86 is placed against the bottom of the interior cavity surface of the reusable mold 82. The predetermined contoured surface 84 of the positive image form 86 is formed by one of the following methods: If an exact contour of a patient's knee is to be utilized, a female image of that knee is obtained, as described above, by casting an image using plaster, followed by making a disposable rigid male copy fabricated from a rigid epoxy or rigid urethane copy to produce the predetermined contoured surface 84. A second method and a more sophisticated non contact procedure would utilize laser imaging and "3 D Modeling" to fabricate the predetermined contoured surface 84. A series of generic knee shapes could also be fabricated and used to produce a number of predetermined contoured surface 84 shapes for inclusion in a library of contoured shapes from which a patient or orthotist could select a best fit. The first step is to place a predetermined contoured shape 84 into the reusable mold 82 as described above. The height of the composite progressive resistance knee pad 10 is held to a range with upper and lower limits that will insure that the liquid component inlet tube 94 and the liquid component relief tube 98 are clear of interference. The value of T is determined as characterized above. The height of the predetermined contoured shape 84 is then measured and adjusted or the position of the stop flange 92 is adjusted to obtain a progressive resistance knee pad 10 with a predetermined height having a value T.

A cushion layer 22 blank is fabricated and placed into the mold. As in the previous alternative method, a blank for the cushion layer 22 is typically cut from a piece of the desired Durometer sheet stock. The blank will of necessity have to be cut in an ellipsoid shape since it will be placed into cavity 96 or cylinder of the reusable mold 82 at an angle to the center line of the cylinder or cavity 96 instead of perpendicular to the center line. By cutting an ellipsoid shape and cutting the blank slightly oversize, and placing the cushion layer contact surface 24 against the predetermined contoured surface 84, friction along the perimeter of the cushion layer and the inside wall of the reusable mold 82 will hold the cushion layer contact surface 24 of the cushion layer 22 in place against the positive image form 86.

Although not illustrated, it may be advantageous to have a pattern of vacuum drill holes (not shown) passing from the base of the a positive image form 86 to the predetermined contoured surface 84 and coupling the vacuum drill holes to a vacuum source that would suck the cushion layer 22 against the predetermined contoured surface 84 and hold it uniformly against the surface during the following molding process.

The next step in the fabrication procedure is to fasten or loosely couple the base layer mounting surface 40 of a previously assembled base layer 12 with its imbedded mounting plate 14 to the cavity termination surface 89 of the retention ram 90. The use of a vacuum source and ports through the retention ram 90 to the vacuum source are a possible means for the attachment of the base layer to the retention ram 90. A magnet in the cavity termination surface 89 of the retention ram 90 capable of attracting the imbedded mounting plate 14 is another alternative embodiment for attaching the base layer 12 to the retention ram 90. Registration of the base layer on the retention ram and registration of the retention ram 90 with the predetermined contoured surface 84 is within the skill of the technicians using the equipment.

The retention ram 90 with the attached base layer 12 is inserted into the reusable mold 82 using the previously described threads on the stop flange 92 corresponding to threads on the retention ram 90, shims, threads, stepped incline shims or other means of controlling the axial travel of the retention ram 90 to obtain the predetermined value of T as shown in FIGS. 2 and 8 at the conclusion of the molding process.

Rotational orientation of the base layer 12 is required if a predrilled and tapped mounting plate 20 is imbedded in the base layer 12 so as to align a pair of the threaded screw holes 16a, 16b and 16c with the forward most point of the cushion layer 58 when the progressive resistance knee pad is attached to the knee brace. Generic mounting plates like those imbedded in after market knee pads such as those supplied by orthotists with no mounting holes, would not require rotational orientation.

A cavity is now in place between the cushion layer support surface 26 of the cushion layer 22 and the base layer top surface 38 of the base layer 12, and injection of the material for the middle layer 28 into the void space is started.

The material selected for injection is Dow Corning 3-8159 RF Silicone Foam, a two part product which when thoroughly mixed in a 1:1 ratio produces a foamed elastomer in approximately 10 minutes at room temperature. The shortened period for curing provides this second method with a distinct commercial advantage over the above method using a disposable mold and which has a ten day drying period. The Dow Corning 3-8159 RF Silicone Foam adheres to silicone products such as the cushion layer 22 and the urethane base layer 12.

The cured product has a quoted Durameter value of 65-70 on the Shore 00 scale which equates to approximately a Durameter value of 37 on the Shore A scale, the quoted value for the Dow Corning 739 Plastic Adhesive described earlier, giving the middle layer 28 of the Progressive resistance knee pad 10 similar properties regardless of the manufacturing procedure, with the cushion layer 22 and the base layer 12 being the same for either procedure.

In order to obtain the published properties, the liquid components of the Dow Corning 3-8159RF Silicone Foam is pumped and metered in a 1:1 ratio into the mixing device and pumped through the liquid component inlet tube 94 of the reusable mold 82 into the aforementioned cavity between the cushion layer support surface 26 and the base layer top surface 38 of the base layer 12 forcing out the trapped air until liquid flows from the mold relief tube 98. Referring to FIG. 8, once the foamed elastomer has cured, the vacuum sources are disconnected if used, the ejection rod 88 drives the base of the positive image form 86 and retention ram 90 with the cured progressive resistance knee pad there-between, to the right. The motion shears the cured material at the liquid component mix inlet tube 94 and the relief tube 98 as to force the entire contents of the reusable mold 82. The completed Progressive resistance knee pad 10 article is then separated from the positive image form 86 and the retention ram 90 which are then available for reuse. The liquid component mix inlet tube 94 and the relief tube 98 may be lined with disposable and replaceable tubes to aid in clean-up and reuse of the reusable mold 82.

In view of the foregoing, the scope of the present invention should not be limited to the particular embodiments described and illustrated herein, as they are intended to be exemplary in nature. The scope of the present invention should be fully commensurate with that of the claims appended hereafter and their functional equivalents.

APPENDIX

GLOSSARY OF TERMS

| Reference Number | Figure | Element Name |
| --- | --- | --- |
| 10 | 1, 2, 4,, | progressive resistance knee pad |
| 12 | 2, 8 | base layer |
| 14 | | imbedded mounting plate |
| 16a, b, c | 1, 3, 4 | threaded screw holes |
| 18a, 18b, 18c | | post mooring holes |
| 20 | 2, 4 | hinge housing |
| 22 | 2, 8 | cushion layer |
| 24 | 2, 8 | cushion layer contact surface |
| 26 | 2, | cushion layer support surface |
| 28 | 2, 5d, 5e | middle layer |
| 30 | 2, 8 | middle layer mating surface |
| 34 | 2, 8 | middle layer base surface |
| 38 | | base layer top surface |
| 40 | | base layer mounting surface |
| 42 | 3 | Inner hinge cover |
| 44 | 3 | Outer hinge cover |
| 46 | | proprietary geared relationship |
| 50 | 3 | upper articulating arm |
| 52 | 3 | lower articulating arm |
| 53a, 53b | 2 | threaded screws, |
| 58 | | forward most point of the cushion layer, |
| 64 | | forward edge or forward most point of the right leg hinge housing, |
| 66 | | orthotic support appliance |
| 68 | | disposable positive image form |
| 70 | | negative image form |
| 73 | | cup mold lip |
| 74 | | disposable cup mold |
| 75 | | exposed surface of the fast drying material |
| 76 | 6,7 | threads (nylon) |
| 78 | 6,7 | holes (in cup) |
| 82 | 8 | reusable mold |
| 84 | 8 | predetermined contoured surface |
| 86 | 8 | positive image form |

APPENDIX-continued

GLOSSARY OF TERMS

| Reference Number | Figure | Element Name |
| --- | --- | --- |
| 88 | 8 | Ejection rod |
| 89 | 8 | Retention ram cavity termination surface |
| 90 | 8 | Retention ram |
| 92 | 8 | stop flange |
| 94 | 8 | inlet tube |
| 96 | 8 | cavity |
| 98 | 8 | relief tube |

What is claimed is:

1. A progressive resistance knee pad coupled to the inner surfaces of an orthotic support appliance (a knee brace) to prevent metal components of an orthotic support from contacting clothing, tissue or skin surface of the wearer of the orthotic support appliance comprising:
   a cushion layer having a contoured contact surface and a support surface,
   a middle layer having a mating surface and a base surface,
   a base layer, the base layer having a top surface and a mounting surface,
   and an imbedded mounting plate imbedded in the base layer,
   the cushion layer being formed from a first predetermined Durometer material, and having a uniform thickness,
   the middle layer being formed from a second predetermined Durometer material having a lower Durometer value than the base layer, the middle layer being formed as a homogenous and void free layer having a varying cross section, the middle layer mating surface being contiguous and congruent with and bonded to the cushion layer support surface, the middle layer mating surface being formed to shape the cushion layer contact surface to conform with a predetermined contoured surface, the thickness of the middle layer being controlled and adjusted to provide a substantially planar base surface,
   the base layer top surface being contiguous and congruent with and bonded to the middle layer base surface,
   the base layer imbedded mounting plate having a plurality of threaded holes for receiving screws from the inner surfaces of the knee brace for coupling the progressive resistance knee pad to the orthotic support appliance and,
   a plurality of post mooring holes that permit the material forming the base layer to pass through the post mooring holes and around the imbedded mounting plate to support the imbedded mounting plate from moving within the base layer.

2. The progressive resistance knee pad of claim 1 wherein the middle layer is further characterized as being formed from a material having a Durometer value material that is higher in Durometer value than the Durometer value of the material of the cushion layer.

3. The progressive resistance knee pad of claim 1 wherein the base layer is further characterized as being formed from urethane.

4. The progressive resistance of the knee pad of claim 1 wherein the imbedded mounting plate is formed from metal, the imbedded mounting plate having a plurality of locations for receiving fasteners that couple it to the inner surfaces of the knee brace.

5. The progressive resistance of the knee pad of claim 1 wherein the imbedded mounting plate has a plurality of threaded screw holes for receiving threaded screws from the inner surfaces of the knee brace.

6. A method of making a progressive resistance knee pad coupled to the inner surfaces of a knee brace forming an orthotic support appliance comprising the steps of:

providing a cushion layer having a contoured contact surface and a uniform thickness, providing a middle layer to hold the cushion layer in a contoured shape, the Durometer material of the middle layer being harder than the Durometer material of the cushion layer, bonding the middle layer to the cushion layer, providing a base layer, with an imbedded mounting plate imbedded in the base layer, the Durometer material of the base layer being harder than the Durometer material of the middle layer, the base layer and the imbedded mounting plate being formed to have a base layer top surface contiguous and congruent with and bonded to the middle layer base surface, the imbedded mounting plate also being formed to have a plurality of post mooring holes that permit the material forming the base layer to pass through the post mooring holes and around the imbedded mounting plate to support the imbedded mounting plate from moving within the base layer, and a plurality of threaded holes for receiving screws from the inner surfaces of the knee brace for coupling the progressive resistance knee pad to the orthotic support appliance, bonding the base layer to the middle layer to form a composite structure, attaching the progressive resistance knee pad to the knee brace and orientating the progressive resistance knee pad on the support appliance to prevent metal components of the knee brace from contacting clothing, tissue or skin surface of the wearer.

7. The method of claim 6 wherein the step of bonding the middle layer to the cushion layer further comprises the steps of:

providing a disposable container partially filled with a liquefied quick-setting casting material, providing a casting of the patients knee with a releasable surface and impressing the releasable surface into the liquefied quick-setting casting material to a depth and for a period of sufficient duration for the releasable surface to transfer and form a positive image form of a portion of the patient's knee that will receive the a contact surface of the progressive resistance knee pad to the liquefied quick-setting casting material at a depth in the disposable container leaving a remainder space for the formation of a middle layer followed by a base layer, positioning the cushion layer in the container tightly on the positive mold of the patient's knee, pouring a middle layer material having a Durometer value that is higher in Durometer value than the Durometer value of the material of the cushion layer into the disposable container and onto the cushion layer, providing a base layer with an imbedded mounting plate formed from a material having a Durometer value that is higher in Durometer value than the Durometer value of the material of the middle layer, and positioning the base layer in the cushion layer to a predetermined build height.

8. The method of claim 6 wherein the step of providing a base layer, with an imbedded mounting plate imbedded in the base layer, further comprises the steps of:

providing a mounting plate blank, the mounting plate blank having threaded screw holes and one or more post mooring holes, providing a mold in which the base layer will be molded, feeding or pouring a predetermined quantity of base layer urethane material into the mold, positioning the mounting plate at a predetermined and uniform depth in the mold; the base layer urethane material passing through the one or more post mooring holes to stabilize the location of the mounting plate in the base layer, feeding or pouring a final amount of base layer urethane material into the mold to obtain a base layer with a predetermined final thickness.

9. The method of claim 6 wherein the step of bonding the middle layer to the cushion layer further comprises the steps of:

looping an array of threads over the cushion layer, through the walls of the disposable container and around a disposable container base to tightly draw the cushion layer to a positive image form surface.

10. A method of making a progressive resistance knee pad coupled to the inner surfaces of a knee brace to form an orthotic support appliance, the progressive resistance knee pad preventing metal components of the knee brace from contacting clothing, tissue or skin surface of the wearer using a method comprising the steps of:

providing a molding fixture with a with a cavity having a first inner surface shaped as a positive image of a patient's knee within the cavity, inserting a cushion layer having a contact surface and a uniform thickness into the cavity, the cushion layer contact surface being positioned against the first inner surface, providing a retention ram having a retention ram cavity termination surface, providing a base layer, with an imbedded mounting plate imbedded in the base layer, attaching the base layer to the retention ram cavity termination surface, inserting the retention ram with the attached base layer into the mold cavity with the retention ram cavity termination surface orientated to move the base layer toward the positive image within a mold cavity, to a predetermined depth allowing space for a middle layer cavity to remain in the mold cavity between the base layer and the cushion layer, injecting a premixed two component silicon elastomer into the middle layer cavity in the mold cavity to fill the middle layer cavity.

11. The progressive resistance knee pad of claim 10 wherein the steps for making the progressive resistance knee pad further comprise:

inserting a removable positive image form having a first inner surface shaped as a positive image of a patient's knee into the cavity to supply the first inner surface shaped as a positive image of a patient's knee.

12. The progressive resistance knee pad of claim 10 wherein the steps for making the progressive resistance knee pad further comprise:

providing the molding fixture cavity with a liquid component injection tube on a first cavity wall at a location central to the middle layer cavity to guide the premixed two component silicon elastomer into the middle layer cavity, and providing the molding fixture cavity with a mold component relief tube to vent excess premixed two component silicon elastomer from the middle layer cavity as the premixed two component silicon elastomer is driven into the middle layer cavity under pressure to eliminate all void space from the middle layer cavity.

13. The progressive resistance knee pad of claim 10 wherein the steps for making the progressive resistance knee pad further comprise:

providing the base layer with a material having a Durometer value that is higher in Durometer value than the Durometer value of the material of the middle layer.

14. The progressive resistance knee pad of claim 10 wherein the steps for making the progressive resistance knee pad further comprise:

providing the middle layer with a material having a Durometer value that is higher in Durometer value than the Durometer value of the material of the cushion layer.

15. The progressive resistance knee pad of claim 10 wherein the steps for making the progressive resistance knee pad further comprise:

forming the base layer from urethane.

\* \* \* \* \*